(12) United States Patent
Ionkin et al.

(10) Patent No.: US 7,718,997 B2
(45) Date of Patent: May 18, 2010

(54) TETRASUBSTITUTED CORONENES

(75) Inventors: Alex Sergey Ionkin, Kennett Square, PA (US); Ying Wang, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 711 days.

(21) Appl. No.: 11/580,386

(22) Filed: Oct. 13, 2006

(65) Prior Publication Data

US 2008/0087879 A1    Apr. 17, 2008

(51) Int. Cl.
*H01L 51/00* (2006.01)
*H01L 51/50* (2006.01)
*H01L 51/54* (2006.01)
*C07C 15/00* (2006.01)
*C07C 15/20* (2006.01)

(52) U.S. Cl. .................. 257/40; 257/E51.049; 585/26; 313/504; 313/506; 428/690; 428/917; 136/263

(58) Field of Classification Search .................. 257/40, 257/E51.049; 585/26; 313/504, 506; 428/690, 428/917; 136/263
See application file for complete search history.

(56) References Cited

U.S. PATENT DOCUMENTS 7,148,508 B2 * 12/2006 Miyazawa .................. 257/72

FOREIGN PATENT DOCUMENTS

| JP | 2006004721 A2 | | 1/2006 |
| WO | WO03026359 | * | 3/2003 |
| WO | 2006023369 A1 | | 3/2006 |

OTHER PUBLICATIONS

Abstract From ESP@CENET for JP2006004721A2.
Ruifeng Zhang et al., Blue Light-Emitting Diodes Based on Coronene-Doper Polymers, Synthetic Materials, vol. 105 (1999), pp. 49-53.
T. Sano et al., Organic Electroluminescent Devices Doped With Condensed Polycyclic Aromatic Compounds, Synthetic Metals, vol. 91 (1999), pp. 27-30.

* cited by examiner

*Primary Examiner*—Duc Truong
(74) *Attorney, Agent, or Firm*—Gail D. Tanzer

(57) ABSTRACT

Tetrasubstituted coronenes are provided. Also provided are electronic devices in which the active layer includes a tetra-substituted coronene.

8 Claims, 1 Drawing Sheet

Schematic of a light-emitting device

Figure 1 – Schematic of a light-emitting device
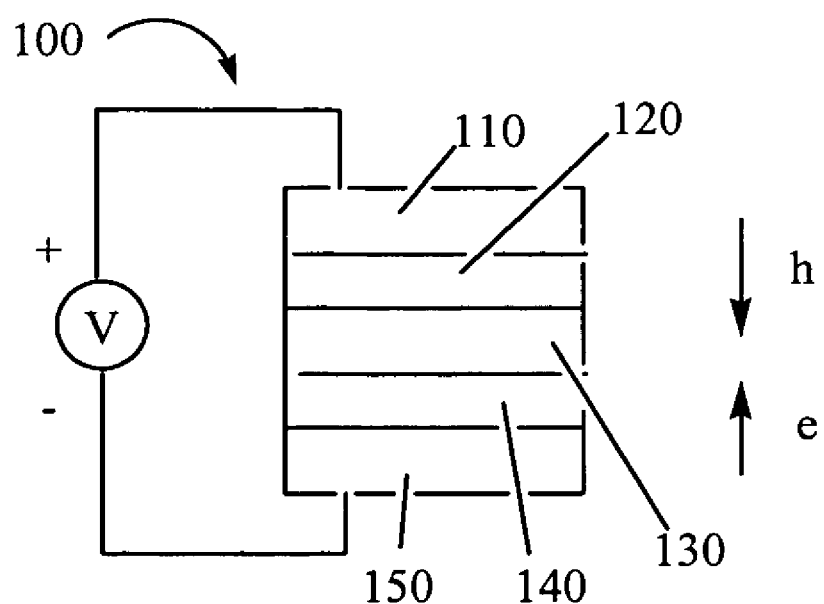

US 7,718,997 B2

TETRASUBSTITUTED CORONENES

FIELD OF THE INVENTION

The present invention is directed to tetrasubstituted coronenes. The invention is further directed to electronic devices in which the active layer includes a tetrasubstituted coronene.

BACKGROUND

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Such polycyclic aromatic compounds due to their rigid structures possess attractive properties such as high thermostability (e.g., melting points are often above 400° C.) and good stability to photo-oxidation, which lead to LED devices with longer lifetimes.

However, there is a continuing need for electroluminescent compounds.

SUMMARY OF THE INVENTION

One aspect of this invention is a composition represented by Formula I:

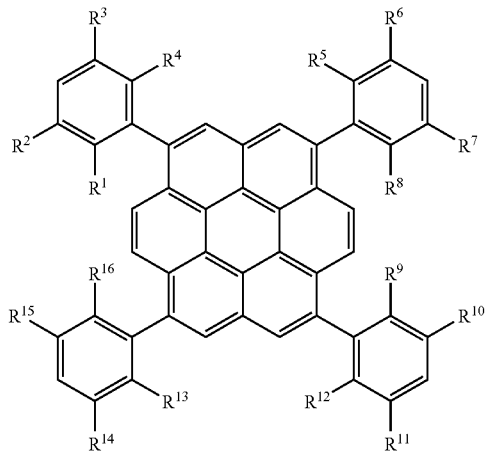

Formula I wherein:
$R^1$-$R^{16}$ are independently selected from the group consisting of H, F, alkyl, aryl, fluoroalkyl, fluoroaryl, and $E(R^9)_3$ groups wherein E is Si, Ge, or Sn, wherein at least one of $R^1$-$R^4$, at least one of $R^5$-$R^8$, at least one of $R^9$-$R^{12}$ and at least one of $R^{13}$-$R^{16}$ is not H or F.

A further aspect of the present invention is an electronic device having at least one emitting layer comprising at least one compound of Formula I.

DESCRIPTION OF THE DRAWINGS

FIG. 1 is a schematic diagram of a light-emitting device (LED).

DETAILED DESCRIPTION

As used herein with regard to groups within chemical formulas, "alkyl" refers to saturated hydrocarbon chains. Preferred alkyl groups include those having carbon chain lengths of 1 to 20 carbons, more preferably 1 to 10 carbon atoms. Examples of preferred alkyl groups include methyl, ethyl, propyl, iso-propyl, butyl, iso-butyl, t-butyl, neo-pentyl, neo-octyl As used herein with regard to groups within chemical formulas, "aryl" refers to moieties comprising at least one aromatic ring, which can be substituted or unsubstituted. An aryl can have one or more aromatic rings that can be fused, connected by single bonds or other groups. Examples of substituent groups that can be on substituted aromatic rings in the compounds having the formulas disclosed herein include $C_1$-$C_{20}$ alkyl, $C_6$-$C_{10}$ aryl, silyl, F, Cl and Br.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

In one embodiment, the present invention is directed to coronenes represented by Formula I:

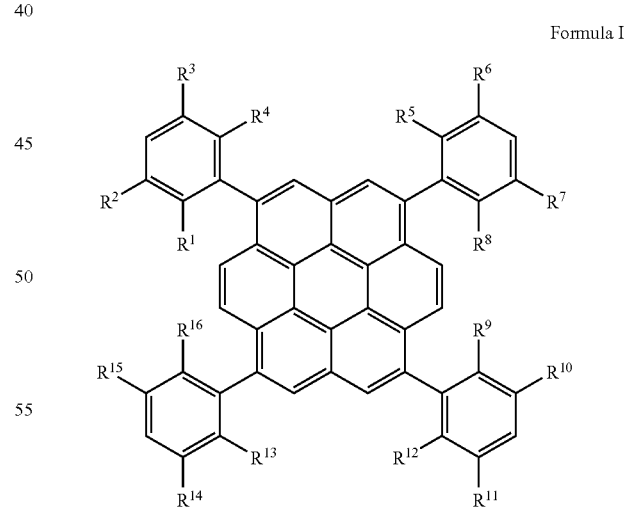

Formula I wherein:
$R^1$-$R^{16}$ are independently selected from the group consisting of H, F, alkyl, aryl, fluoroalkyl, fluoroaryl, and $E(R^9)_3$ groups wherein E is Si, Ge, or Sn, wherein at least one of $R^1$-$R^4$, at least one of $R^5$-$R^8$, at least one of $R^9$-$R^{12}$ and at least one of $R^{13}$-$R^{16}$ is not H or F.

The alkyl and aryl groups of $R^1$-$R^{16}$ can be optionally partially or completely fluorinated.

In one embodiment of this invention, $R^1$, $R^4$, $R^5$, $R^8$, $R^9$, $R^{12}$, $R^{13}$ and $R^{16}$ are methyl, and $R^2$, $R^3$, $R^6$, $R^7$, $R^{10}$, $R^{11}$, $R^{14}$ and $R^{15}$ are H. In another embodiment, $R^1$, $R^4$, $R^5$, $R^8$, $R^9$, $R^{12}$, $R^{13}$ and $R^{16}$ are H and $R^2$, $R^3$, $R^6$, $R^7$, $R^{10}$, $R^{11}$, $R^{14}$ and $R^{15}$ are $CF_3$.

In one embodiment, the compositions of Formula I exhibit blue phosphorescence. In one embodiment, the complexes have photoluminescent and/or electroluminescent spectra that have a maximum emission between 440 nm and 460 nm.

The coronene compositions of this invention are neutral and non-ionic, and can be sublimed intact. Thin films of these materials obtained via sublimation or vacuum deposition exhibit good to excellent electroluminescent properties. Introduction of fluorine substituents increases the volatility of the compositions. As a result, vacuum deposition can be carried out at lower temperatures and decomposition of the compositions can be avoided. Introduction of fluorine substituents can often reduce the non-radiative decay rate and the self-quenching phenomenon in the solid state. These reductions can lead to enhanced luminescence efficiency.

The substituted coronenes can be prepared, for example, using Ru-catalyzed benzannulations (as described by H. C.-Shen et al., J. Org. Chem. (2005), 70(24), 10113-10116), or by acetylation (as described by M. A. Quershi et al., Sind University Research Journal, Science Series (1984), Volume Date 1983, 15 67-72).

Another embodiment of this invention is an electronic device comprising at least one photoactive layer positioned between two electrical contact layers, wherein the at least one layer of the device includes the composition of Formula I. Devices frequently have additional hole-transport and electron-transport layers. A typical structure is shown in FIG. 1. The device 100 has an anode layer 110 and a cathode layer 150. Adjacent to the anode is a layer 120 comprising hole-transport material. Adjacent to the cathode is a layer 140 comprising an electron-transport material. Between the hole-transport layer and the electron-transport layer is the photoactive layer 130.

Depending upon the application of the device 100, the photoactive layer 130 can be a light-emitting layer that is activated by an applied voltage (such as in a light-emitting diode or light-emitting electrochemical cell), a layer of material that responds to radiant energy and generates a signal with or without an applied bias voltage (such as in a photodetector). Examples of photodetectors include photoconductive cells, photoresistors, photoswitches, phototransistors, phototubes, and photovoltaic cells, as these terms are described by John Markus in *Electronics and Nucleonics Dictionary*, 470 and 476 (McGraw-Hill, Inc. 1966).

The coronene compositions can be used as the light-emitting material in diodes. Additional materials can be present in the emitting layer with the coronene. A diluent or host material can also be added. Suitable diluents include charge transport materials, processing aids and inert matrix materials. The diluent can include polymeric materials, small molecules or mixtures thereof. The diluent may improve the physical or electrical properties of films containing the coronene compound, may decrease self-quenching in the coronene compounds described herein, and/or may decrease the aggregation of the coronene compounds described herein. Non-limiting examples of suitable polymeric materials include poly(N-vinyl carbazole) and polysilane. Non-limiting examples of suitable small molecules includes 4,4'-N,N'-dicarbazole biphenyl and tertiary aromatic amines. When a diluent is used, the coronene composition is generally present in a small amount. In one embodiment, the amount of coronene composition in the photoactive layer is less than 20% by weight, based on the total weight of the layer; in another embodiment, the coronene composition is less than 10% by weight.

The other layers in the OLED can be made of any materials suitable for use in each of such layers. The anode 110, is an electrode that is particularly efficient for injecting positive charge carriers. For example, it can be made of materials containing a metal, mixed metals, alloys, metal oxides or mixed-metal oxides, or it can be a conducting polymer. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The IUPAC numbering system is used throughout, where the groups from the Periodic Table are numbered from left to right as 1-18 (CRC Handbook of Chemistry and Physics, $81^{st}$ Edition, 2000). The anode 110 may also comprise an organic material, such as polyaniline, as disclosed in "Flexible light-emitting diodes made from soluble conducting polymer," *Nature* vol. 357, pp 477-479 (11 Jun. 1992). At least one of the anode and cathode is desirably at least partially transparent to allow the generated light to be observed.

Examples of hole-transport materials for layer 120 have been summarized for example, in Kirk-Othmer Encyclopedia of Chemical Technology, Fourth Edition, Vol. 18, p. 837-860, 1996, by Y. Wang. Both hole-transporting molecules and polymers can be used. Commonly used hole-transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), and porphyrinic compounds, such as copper phthalocyanine. Commonly used hole-transporting polymers are polyvinylcarbazole, (phenylmethyl)polysilane, and polyaniline. It is also possible to obtain hole-transporting polymers by doping hole-transporting molecules such as those mentioned above into polymers such as polystyrene and polycarbonate.

Examples of electron-transport materials for layer 140 include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer 140 can function both to facilitate electron-transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing organometallic compounds can also be deposited between the organic layer and the cathode layer to lower the operating voltage.

It is known to have other layers in organic electronic devices. For example, there can be a layer (not shown) between the conductive polymer layer 120 and the active layer 130 to facilitate positive charge transport and/or band-gap matching of the layers, or to function as a protective layer. Similarly, there can be additional layers (not shown) between the active layer 130 and the cathode layer 150 to facilitate negative charge transport and/or band-gap matching between the layers, or to function as a protective layer. Layers that are known in the art can be used. In addition, any of the above-described layers can be made of two or more layers. Alternatively, some or all of inorganic anode layer 110, the conductive polymer layer 120, the active layer 130, and cathode layer 150, can be surface-treated to increase charge carrier transport efficiency. The choice of materials for each of the component layers is preferably determined by balancing the goals of providing a device with high device efficiency. Each functional layer can be made up of more than one layer.

The device can be prepared by sequentially vapor-depositing the individual layers on a suitable substrate. Substrates such as glass and polymeric films can be used. Conventional vapor deposition techniques can be used, such as thermal evaporation and chemical vapor deposition. Alternatively, the organic layers can be coated from solutions or dispersions in suitable solvents, using any conventional coating technique. In general, the different layers will have the following range of thicknesses: anode 110, 500-5000 Å, preferably 1000-2000 Å; hole-transport layer 120, 50-1000 Å, preferably 200-800 Å; light-emitting layer 130, 10-1000 Å, preferably 100-800 Å; electron-transport layer 140, 50-1000 Å, preferably 200-800 Å; cathode 150, 200-10000 Å, preferably 300-5000 Å. The location of the electron-hole recombination zone in the device, and thus the emission spectrum of the device, can be affected by the relative thickness of each layer. Thus the thickness of the electron-transport layer is desirably chosen so that the electron-hole recombination zone is in the light-emitting layer. The desired ratio of layer thicknesses can be determined by one skilled in the art, based on the nature of the materials used.

The efficiency of devices made with the coronene compounds disclosed herein can be further improved by optimizing the other layers in the device. For example, more efficient cathodes such as Ca, Ba or LiF can be used. Shaped substrates and novel hole-transport materials that result in a reduction in operating voltage or increase quantum efficiency are also applicable. Additional layers can also be added to tailor the energy levels of the various layers and facilitate electroluminescence.

EXAMPLES

The following examples illustrate certain features and advantages of the present invention. They are intended to be illustrative of the invention, but not limiting. All percentages are by weight, unless otherwise indicated.

The following chemicals used in the Examples below were purchased from Sigma-Aldrich Inc. (St. Louis, Mo.): dimethylphenyl boronic acid; 3,5-bistrifluoromethyl-phenylboronic acid; cesium carbonate; tris(dibenzylideneacetone)dipalladium(0).

Di-tert-butyl-trimethylsilylmethyl-phosphane ($^tBu_2P$—$CH_2$—$SiMe_3$) was prepared as follows: 50.00 g (0.277 mol) of di-tert-butylchlorophosphine, 304 ml of a 1.0 M pentane solution of (trimethylsilylmethyl)lithium and 150 ml of THF were refluxed under argon for 3 days. The reaction mixture was allowed to cool to room temperature, and then an aqueous solution of ammonium chloride was added slowly. The organic phase was separated, and dried over magnesium sulfate. After removal of the solvent, the product was purified by distillation in vacuum. The yield of di-tert-butyl-trimethylsilanylmethyl-phosphane was 55.32 g (86%) with b.p. 50-52° C./0.5 mm. $^{31}$P-NMR ($C_6D_6$)+20.05 ppm. $^1$H NMR ($C_6D_6$) 0.01 (s, 9H, $SiMe_3$), 0.23 (d, 2H, $^2J_{PH}$=5.34 Hz, P—$CH_2$—$SiMe_3$), 0.91 (s, 9H, $Me_3C$), 0.93 (s, 9H, $Me_3C$). Anal. Found: C, 61.89; H, 12.53; P, 13.25.

1,4,7,10-Tetrabromo-coronene

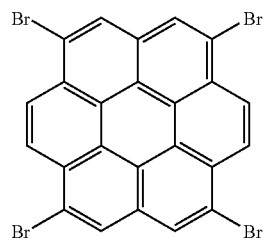

Bromine (15.60 g, 0.0976 mol) in trimethylphosphate (200 ml) was added dropwise to a stirred solution of coronene (2.5 g, 0.0083 mol) dissolved in trimethylphosphate (200 ml) at 60° C. The reaction temperature was slowly increased to 120° C. and kept for 5 days at that temperature. The resultant precipitate was filtered and washed with methanol (2×100 ml) and hexane (2×100 ml). Yield of 1,4,7,10-tetrabromo-coronene was 5.13 g (96.88%). Direct probe GC/MS Exact mass found for $C_{24}H_8Br_4$ is 611.74 g/mole. Calculated for $C_{24}H_8Br_4$ is 611.74.

Example 1

1,4,7,10-Tetrakis-(2,6-dimethyl-phenyl)-coronene

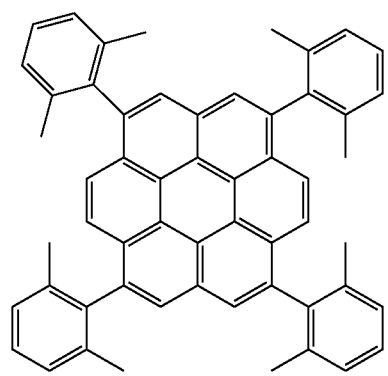

4.9 g (0.00795 mol) of 1,4,7,10-tetrabromo-coronene as prepared above 5.73 g (0.0382 mol) of 2,6-dimethylphenyl boronic acid, 0.87 g (0.00095 mol) of tris(dibenzylideneacetone) dipalladium (0), 0.53 g (0.00228 mol) of di-tert-butyltrimethylsilylmethyl-phosphane, 12.45 g (0.0382 mol) of cesium carbonate and 100 ml of dioxane were refluxed under argon for 24 hr. The resulted mixture was poured into 200 ml of water and extracted twice by 200 ml of methylene chloride. The organic phase was dried with magnesium sulfate overnight and filtered. The solvent was removed on rotary evaporator and the residue was purified by chromatography on silica gel using petroleum ether/ethyl ether (10/0.5). Yield of 1,4,7,10-tetrakis-(2,6-dimethyl-phenyl)-coronene was 2.20 g (38.60%) as a yellow solid with no m.p. below 200° C. $^1$H NMR (CD$_2$Cl$_2$) 1.90-2.05 (multiplets, 24H, Me), 7.10-7.40 (multiplets, 12H, arom-H), 8.05-8.55 (multiplets, 4H, arom-H), 8.70-9.10 (multiplets, 4H, arom-H). GC/MS (direct probe), found: 716.34. The structure was confirmed by X-ray analysis. The photoluminescence of 1,4,7,10-tetrakis-(2,6-dimethyl-phenyl)-coronene displays a maximum emission at 440 nm in methylene chloride solution.

Example 2

1,4,7,10-Tetrakis-(3,5-bis-trifluoromethyl-phenyl)-coronene

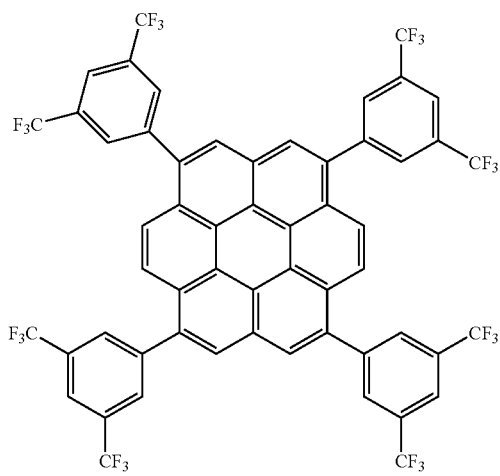

5.0 g (0.00812 mol) of 1,4,7,10-tetrabromo-coronene, 11.64 g (0.0451 mol) of 3,5-bis-trifluoromethylphenyl boronic acid, 1.03 g (0.001124 mol) of tris(dibenzylideneacetone) dipalladium (0), 0.63 g (0.00271 mol) of di-tert-butyl-trimethylsilylmethyl-phosphane, 14.70 g (0.0451 mol) of cesium carbonate and 100 ml of dioxane were refluxed under argon for 24 hr. The resulted mixture was poured into 200 ml of water and extracted twice by 200 ml of methylene chloride. The organic phase was dried over magnesium sulfate overnight and filtered. The solvent was removed on rotary evaporator and the residue was purified by chromatography on silica gel with petroleum ether/ethyl ether (10/0.5). Yield of 1,4,7,10-tetrakis-(3,5-bis-trifluoromethyl-phenyl)-coronene was 5.78 g (61.95%) as a yellow solid with no m.p. below 200° C. $^1$H NMR (CD$_2$Cl$_2$) 8.15-9.00 (multiplets, 20H, arom-H, GC/MS (direct probe) found: 1148.12.

1,4,7,10-tetrakis-(3,5-bis-trifluoromethyl-phenyl)-coronene displays a maximum of emission at 440 nm in methylene chloride solution.

Example 3

OLED devices were fabricated by the thermal evaporation technique. The base vacuum for all of the thin film deposition was in the range of $10^{-8}$ torr. The deposition chamber was capable of depositing twelve different films without the need to break the vacuum.

Patterned indium tin oxide (ITO) coated glass substrates from Thin Film Devices, Inc (Anaheim, Calif.) were used. These ITO's are based on Corning 1737 glass coated with 1400 Å ITO coating, with sheet resistance of 30 ohms/square and 80% light transmission. The patterned ITO substrates were then cleaned ultrasonically in aqueous detergent solution. The substrates were then rinsed with distilled water, followed by isopropanol, and then degreased in toluene vapor.

The cleaned, patterned ITO substrate was then loaded into the vacuum chamber and the chamber was pumped down to $10^{-8}$ torr. The substrate was then further cleaned using an oxygen plasma for about 1.5 min. After cleaning, multiple layers of thin films were then deposited sequentially onto the substrate by thermal evaporation. Patterned metal electrodes (Al or LiF/Al) or bipolar electrode were deposited through a mask. The thickness of the film was measured during deposition using a quartz crystal monitor. All organic film thickness reported in the Examples is nominal, calculated assuming the density of the material deposited to be one. The completed OLED device was then encapsulated in a glove box using a glass lid and epoxy.

The OLED samples were characterized by measuring their (1) current-voltage (I-V) curves, (2) electroluminescence radiance versus voltage, and (3) electroluminescence spectra versus voltage. The I-V curves were measured with a Keithley Source-Measurement Unit Model 237. The electroluminescence radiance (in units of cd/m$^2$) vs. voltage was measured with a Minolta LS-110 luminescence meter while the voltage was scanned using the Keithley SMU. The electroluminescence spectrum was obtained by collecting light using an optical fiber, through an electronic shutter, dispersed through a spectrograph, and then measured with a diode array detector. All three measurements were performed at the same time and controlled by a computer. The efficiency of the device at certain voltage is determined by dividing the electroluminescence radiance of the LED by the current density needed to run the device. The unit is in cd/A.

Table 1 summarizes device configuration and efficiency of OLED devices fabricated using materials disclosed in the present invention. MPMP is the hole transport material and TPBI is the electron transport material. Their molecular structures are shown in the following. The compound was deposited as a neat film. The electroluminescence spectrum shows a peak at 450 nm but with a long tail, presumably due to aggregation in the neat film. This long tail could be removed if the compound is used as guest in a guest-host emitter layer.

Emitter 1:
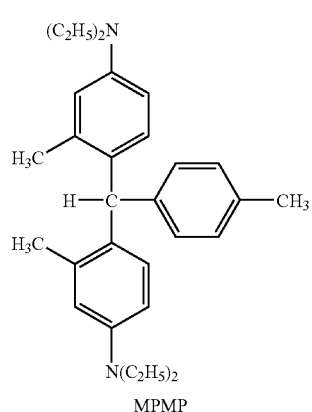
MPMP
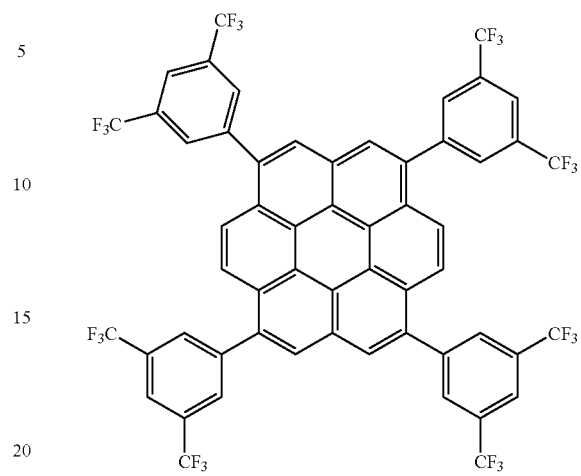
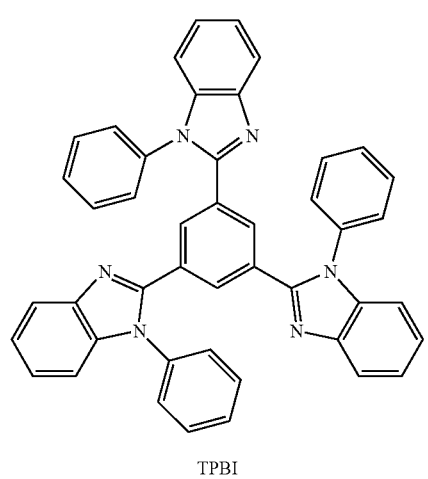
TPBI
Emitter 2:
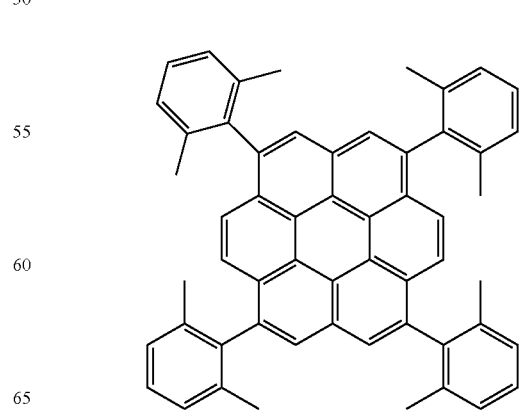

TABLE 1

Device configurations and efficiency of OLED device using coronene emitters

| | Device configuration | Efficiency (cd/A) | Radiance (cd/m$^2$) | Peak wavelength(nm) |
|---|---|---|---|---|
| Example 3.1 (structure shown: coronene with four 3,5-bis(trifluoromethyl)phenyl substituents) | DB(49 nm)/MPMP(30 nm)/ emitter 1(40 nm)/TPBI(30 nm)/ /LiF(1 nm)/Al(100 nm) | 0.8 at 9.5 V | 300 at 15 V | 495 |
| Example 3.2 (structure shown: coronene with four 2,6-dimethylphenyl substituents) | DB(49 nm)/MPMP(30 nm)/ emitter 2(40 nm)/TPBI(30 nm)/ /LiF(1 nm)/Al(100 nm) | 0.65 at 6.5 V | 70 at 15 V | 456 |

What is claimed is:

1. An electronic device comprising at least one layer comprising a compound having Formula I:

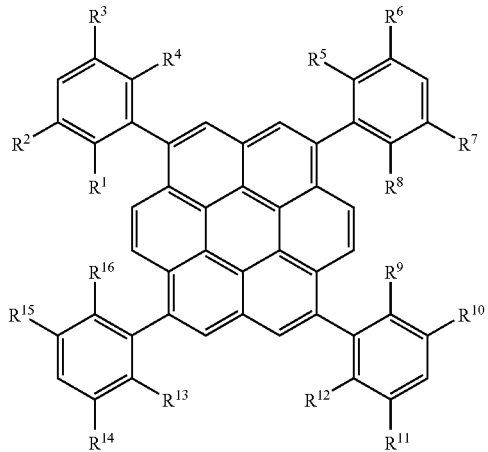

Formula I wherein:
R$^1$-R$^{16}$ are independently selected from the group consisting of H, F, alkyl, aryl, fluoroalkyl, fluoroaryl, and E(R$^9$)$_3$ groups wherein E is Si, Ge, or Sn, wherein at least one of R$^1$-R$^4$, at least one of R$^5$-R$^8$, at least one of R$^9$-R$^{12}$ and at least one of R$^{13}$-R$^{16}$ is not H or F.

2. The device of claim 1, wherein R$^1$, R$^4$, R$^5$, R$^8$, R$^9$, R$^{12}$, R$^{13}$ and R$^{16}$ are methyl, and R$^2$, R$^3$, R$^6$, R$^7$, R$^{10}$, R$^{11}$ and R$^{15}$ are H.

3. The device of claim 1, wherein R$^1$, R$^4$, R$^5$, R$^8$, R$^9$, R$^{12}$, R$^{13}$ and R$^{16}$ are H and R$^2$, R$^3$, R$^6$, R$^7$, R$^{10}$, R$^{11}$, R$^{14}$ and R$^{15}$ are CF$_3$.

4. The device of claim 1, further comprising a diluent selected from the group consisting of poly(N-vinyl carbazole), polysilane, 4,4'-N,N'-dicarbazole biphenyl, and tertiary amines.

5. The device of claim 1, further comprising a hole-transport layer comprising a compound selected from the group consisting of:
N,N'-diphenyl-N,N'-bis(3-methylphenyl)-[1,1'-biphenyl] 4,4'-diamine; 1,1-bis[(di-4-tolylamino)phenyl]cyclohexane; N,N'-bis(4-methylphenyl)-N,N'-bis(4-ethylphenyl)-[1,1'-(3,3'-dimethyl)biphenyl]-4,4'-diamine; tetrakis-(3-methylphenyl)-N,N,N', N'-2,5-phenylenediamine; α-phenyl-4-N,N-diphenylaminostyrene; p-(diethylamino)benzaldehyde diphenylhydrazone; triphenylamine; bis[4-(N,N-diethylamino)-2-methylphenyl](4-methylphenyl)methane; 1-phenyl-3-[p-(diethylamino)styryl]-5-[p-(diethylamino)phenyl] pyrazoline; 1,2-trans-bis(9H-carbazol-9-yl) cyclobutane; N,N,N',N'-tetrakis(4-methylphenyl)-(1,1'-biphenyl)-4,4'-diamine; porphyrinic compounds,
and combinations thereof.

6. The device of claim 1, further comprising an electron-transport layer comprising a compound selected from the group consisting of tris(8-hydroxyquinolato)aluminum; 2,9-dimethyl-4,7-diphenyl-1,10-phenanthroline; 4,7-diphenyl-1,10-phenanthroline; 2-(4-biphenylyl)-5-(4-t-butylphenyl)-1,3,4-oxadiazole; 3-(4-biphenylyl)-4-phenyl-5-(4-t-butylphenyl)-1,2,4-triazole,
and combinations thereof.

7. A composition of Formula I

Formula I wherein:
R$^1$-R$^{16}$ are independently selected from the group consisting of H, F, alkyl, aryl, fluoroalkyl, fluoroaryl, and E(R$^9$)$_3$ groups wherein E is Si, Ge, or Sn, wherein at least one of R$^1$-R$^4$, at least one of R$^5$-R$^8$, at least one of R$^9$-R$^{12}$ and at least one of R$^{13}$-R$^{16}$ is not H or F.

8. The composition of claim 7, wherein the composition is selected from the group of compositions represented by Structures I and II:

Structure I

Structure II

* * * * *